United States Patent
McCleary et al.

(10) Patent No.: US 7,785,771 B2
(45) Date of Patent: Aug. 31, 2010

(54) ASSAY FOR DETERMINATION OF FREE D-GALACTOSE AND/OR L-ARABINOSE

(75) Inventors: Barry V. McCleary, Gelgany (IE); Simon Charnock, Dun Laoghaire (IE)

(73) Assignee: Megazyme IP Limited, Bray, County Wicklow (IE)

( * ) Notice: Subject to any disclaimer, the term of this patent is extended or adjusted under 35 U.S.C. 154(b) by 464 days.

(21) Appl. No.: 11/722,000

(22) PCT Filed: Dec. 17, 2004

(86) PCT No.: PCT/IE2004/000170

§ 371 (c)(1),
(2), (4) Date: Aug. 23, 2007

(87) PCT Pub. No.: WO2006/064487

PCT Pub. Date: Jun. 22, 2006

(65) Prior Publication Data

US 2009/0098586 A1    Apr. 16, 2009

(51) Int. Cl.
*C12Q 1/00* (2006.01)
(52) U.S. Cl. ............... 435/4; 435/26; 435/975
(58) Field of Classification Search ............ 435/4, 435/26, 975
See application file for complete search history.

(56) References Cited

U.S. PATENT DOCUMENTS 4,800,161 A * 1/1989 Ebeling et al. .............. 435/233

5,278,047 A * 1/1994 Lilja et al. .................. 435/14

OTHER PUBLICATIONS

Shapiro F. et al. Determination of Lactose and D-Galactose Using Thio-NAD+ Instead of NAD+. International Dairy J 12(8)667-669, 2002.*
Lobley R. et al. Simultaneous Assessment of Intestinal Permeability . . . Clinical Science 79(2)175-183, 1990.*
H.U. Bergmeyer (Editor-in-Chief): "Methods of Enzymatic Analysis, 3rd, Edition, vol. VI" 1984, Verlag Chemie, Weinheim, DE pp. 104-112.
J. Melrose et al.: "An enzymatic assay of L-arabinose, using beta-D-galactose dehydrogenase: its applciation in the assay of alha-L-arabinofuranosidase." Carbohydrate Research, vol. 118, 1983, pp. 247-253, Nlelsevier Scientific Publishing Company, Amsterdam.
J.A. Beebe et al.: "Galactose mutarotase: purification, characterization,and investigations of two important histidine residues." Biochemistry, vol. 37, No. 42, 1998, pp. 14989-14997 USAmerican Chemical Society, Easton, PA.

* cited by examiner

Primary Examiner—Ralph Gitomer
(74) Attorney, Agent, or Firm—Michael A. Davitz (57) ABSTRACT

The invention provides an assay kit for the measurement of free D-galactose and/or L-arabinose in a sample, the kit comprising galactose mutarotase and (3-galactose dehydrogenase. The kit may further comprise a reagent capable of hydrolysing molecules containing D-galactose and/or L-arabinose, to yield the free mono- or disaccharide so that the kit finds use for determination of not just of free D-galactose and/or L-arabinose but also those molecules as released (or synthesized) from other molecules, including lactose, D-galactose-1-phosphate, galactosyl-sucrose oligosaccharides (such as raffinose), galactan, galactomannan, arabinan and arabinogalactan.

12 Claims, 4 Drawing Sheets

ASSAY FOR DETERMINATION OF FREE D-GALACTOSE AND/OR L-ARABINOSE

CROSS REFERENCE TO RELATED APPLICATIONS

This application claims the benefit of PCT/IE2004/000170, filed on Dec. 17, 2004.

FIELD OF THE INVENTION

The present invention relates to an improved and rapid assay for the determination of D-galactose and L-arabinose. In particular the assay of the invention may be used to assay free D-galactose and free L-arabinose or these monosaccharides as released (or synthesized) from other molecules, such as lactose, D-galactose-1-phosphate, galactosyl-sucrose oligosaccharides (such as raffinose), galactan, galactomannan, arabinan and arabinogalactan.

BRIEF BACKGROUND OF INVENTION

Lactose, or milk sugar, is a white crystalline disaccharide. It is formed in the mammary glands of all lactating animals and is present in their milk. Lactose yields D-galactose and D-glucose on hydrolysis by lactase (β-galactosidase), an enzyme found in gastric juice. People who lack this enzyme after childhood cannot digest milk and are said to be lactose intolerant. Common symptoms of lactose intolerance include nausea, cramps, gas and diarrhea, which begin about 30 minutes to 2 hours after eating or drinking foods containing lactose. Between 30 and 50 million Americans are lactose intolerant. Certain ethnic and racial populations are more widely affected than others. As many as 75 percent of all African-Americans and Native Americans and 90 percent of Asian-Americans are lactose intolerant. The condition is least common among persons of northern European descent. There is thus a need in the food and beverage industry to be able to rapidly and accurately measure lactose levels.

Galactos(a)emia, characterised by the deficiency of one or more enzymes required by an infant to metabolise D-galactose, is a serious and potentially life-threatening disease. If undiagnosed, D-galactose rapidly builds-up in the blood of newborn babies, and can cause cataracts, growth and mental retardation, liver damage and even death. The occurrence of Galactos(a)emia is approximately 1 in 20,000, and tests for the condition form part of a panel of assays performed as part of newborn screening programs. There are two types of enzymatic test used for the diagnosis of Galactos(a)emia; the first is designed to identify the deficiency of galactose-1-phosphate uridyltransferase, the predominant cause of the condition, and the second quantifies total blood D-galactose (comprising free D-galactose and that in the form of D-galactose-1-phosphate), thus identifying Galactos(a)emia regardless of the cause. Once diagnosed, a sucrose based milk formula free of lactose ensures healthy development of the child. There is thus an established and appreciated requirement to rapidly and accurately determine D-galactose in the clinical environment.

Arabinose finds applications in the flavour, food and pharmaceutical industries, for example in controlled Maillard reactions, as a sweetener, and when derivatised as an antiviral agent, respectively. As L-arabinose is one of the most abundant pentoses on earth, much research activity is focused on the di-, oligo- and polysaccharides that contain this monosaccharide, such as arabinooligosaccharides, arabinoxylans, arabinogalactans and arabinans. Thus, there is a general requirement for a simple and rapid test for L-arabinose. Similarly, much research is performed on di-, oligo- and polysaccharides containing D-galactose, such as galactosyl-sucrose oligosaccharides (such as raffinose), galactooligosaccharides, galactans, galactomannans, arabinogalactans, and glycoforms of glycoproteins, and thus there is also a requirement for a simple and rapid test for D-galactose in this area.

There is a large and well established market for the enzymatic determination of free D-galactose and D-galactose as released from lactose, especially in milk and dairy products, but also in many other foodstuffs and materials. Enzymatic methods for the measurement of lactose are well known and are generally based on the hydrolysis of lactose to D-glucose and D-galactose with β-galactosidase followed by determination of either D-galactose or D-glucose. Quantification by measurement of the released D-galactose is greatly preferred, as foodstuffs in general contain much higher levels of free D-glucose than free D-galactose. However, due to an inherent rate limiting factor fundamental to the biochemistry employed, all current products are very slow, taking between 20 and 40 minutes to complete, and optimally require incubation at a high temperature of approximately 40° C., as compared to the optimal time expected/preferred by the modern analyst of between 2 and 5 minutes (and at ambient room temperature). The fundamentals of the currently employed methods for the measurement of free D-galactose and D-galactose as released from lactose and earlier citations can be found in Beutler, H.-O. (1988). Lactose and D-Galactose. In Methods of Enzymatic Analysis (Bergmeyer, H. U., ed.), 3rd ed., Vol. VI, pp. 104-112, VCH Publishers (UK) Ltd, Cambridge, UK. Those for the measurement of free L-arabinose can be found in Sturgeon R. J. (1988). L-Arabinose. Also in Methods of Enzymatic Analysis pp. 427-431.

An enzymatic test kit for lactose and D-galactose, based on the existing traditional methodology using just β-galactose dehydrogenase, is currently offered by Megazyme (cat. no. K-LACGA), as well as Boehringer Mannheim GmbH, Roche (via R-biopharm), and Scil Diagnostics GmbH.

OBJECT OF THE INVENTION

It is thus an object of the invention to provide an assay kit which has a rapid completion time, for the determination of free D-galactose and/or free L-arabinose, or these monosaccharides as released (or synthesized) from other molecules. Those molecules may be lactose, D-galactose-1-phosphate, galactosyl-sucrose oligosaccharides (such as raffinose), galactan, galactomannan, arabinan and arabinogalactan and the like.

It is a further object to provide an assay kit for conducting the above assays at room temperature.

Another object is to provide a cheap and reliable assay kit. A further object is to provide a simple and quantitative assay kit.

In particular it is an object to provide a test kit for the rapid measurement of free D-galactose and D-galactose as released from lactose, in approximately 5 minutes at room temperature.

A yet further particular object is to provide a test kit for the rapid measurement of free D-galactose and D-galactose as released from D-galactose-1-phosphate, both as constituents of blood, in particular that of newborn babies, in approximately 5 minutes at room temperature.

BRIEF SUMMARY OF INVENTION

According to the present invention there is provided a test kit for the measurement of free D-galactose and/or L-arabinose comprising galactose mutarotase and β-galactose dehydrogenase.

The assay kit may further comprise NAD$^+$.

The galactose mutarotase may be selected from GalM derived from *E. coli*, porcine kidney mutarose, or any other mutarotase catalyzing the interconversion of α- and β-D-galactose and/or α- and β-L-arabinose.

The assay kit may further comprise a reagent capable of releasing D-galactose and/or L-arabinose, or in assisting other reagents in releasing D-galactose and/or L-arabinose from larger molecules. The reagent may be an enzyme selected from β-galactosidase, β-galactanase, α-galactosidase, endo-arabinanase, exo-arabinanase, α-L-arabinofuranosidase, acid phosphatase, alkaline phosphatase, β-mannanase, β-mannosidase, β-xylanase, α-glucuronidase, esterase, and xylan acetyl-esterase.

Preferably the kit further comprises a buffer with or without other chemical additives, in the pH range 4.0 to 10.0. For the higher pH values, the buffer may be Tris/HCl buffer containing EDTA.

Suitably the assay kit comprises sufficient galactose mutarotase to give a concentration of at least 0.1 μg/mL in the final assay mixture. Preferably the concentration is at least 1 μg/mL, more preferably at least 3 μg/mL in the final assay mixture.

The kit is suitable for the determination of D-galactose and L-arabinose. In particular, the kit may be used for the determination of free D-galactose and free L-arabinose or these monosaccharides as released (or synthesized) from other molecules, such as lactose, D-galactose-1-phosphate, galactosyl-sucrose oligosaccharides (such as raffinose), galactan, galactomannan, arabinan and arabinogalactan.

This improvement offers the great advantages of requiring less equipment time and staff costs, and no need for inconvenient high temperature incubations, that require additional or more sophisticated equipment.

DETAILED DESCRIPTION OF INVENTION

Example 1

Principle of all Current Products for the Determination of Free D-Galactose and/or L-Arabinose

All currently available test kits for the determination of free D-galactose and/or L-arabinose, or these monosaccharides as released (or synthesized) from other molecules, such as lactose, D-galactose-1-phosphate, galactosyl-sucrose oligosaccharides (such as raffinose), galactan, galactomannan, arabinan and arabinogalactan, are fundamentally the same in terms of reaction biochemistry employed, and contain the following reagents:

1. Buffer at a high pH (e.g. 8.6 with the Megazyme kit)
2. NAD$^+$
3. β-Galactose dehydrogenase
4. Standard sugar solution
5. β-Galactosidase
6. Buffer at a low pH (e.g. 4.5 with the Megazyme kit)

For instance, the Megazyme kit reagents are supplied in 6 bottles as follows:

Bottle 1: Tris/HCl buffer (25 mL, 2 M, pH 8.6) plus EDTA (40 mM) and sodium azide (0.02% w/v) as a preservative.
Bottle 2: NAD$^+$ (96 mg).
Bottle 3: β-Galactose dehydrogenase suspension in 3.2 M ammonium sulphate (2.4 mL, 100 U/mL).
Bottle 4: Galactose standard solution (5 mL, 0.4 mg/mL in 0.02% w/v sodium azide).
Bottle 5: β-Galactosidase suspension (1.2 mL, 4000 U/mL).
Bottle 6: Sodium acetate buffer (25 mL, 2 M, pH 4.5).

Figure 1:
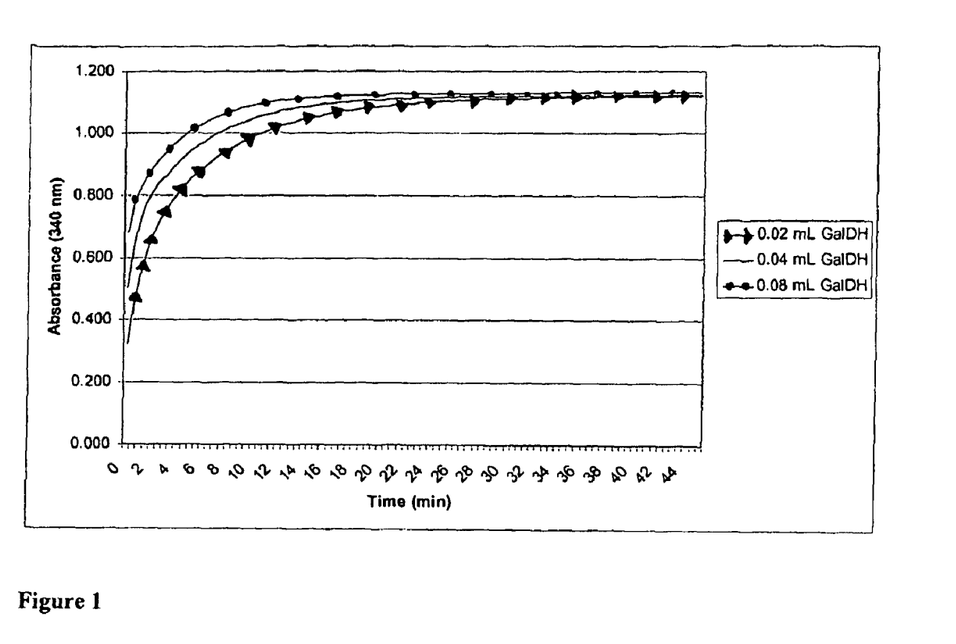
FIG. 1: shows the effect of increasing amounts of β-galactose dehydrogenase in a conventional lactose assay using Megazyme reagents.

The lactose test procedure, for instance, involves mixing an aliquot of sample solution with the low pH buffer and β-galactosidase. After hydrolysis of the lactose to D-galactose and D-glucose (see equation 1), the pH is increased by addition of the high pH buffer, and then after the addition of NAD$^+$ and β-galactose dehydrogenase, galactonic acid and NADH are formed. As NADH absorbs light at 340 nm whereas NAD$^+$ does not significantly, this wavelength is used to monitor progress of the reaction (see equation 2 and FIG. 1). The determination must be quantitative if the results are to be meaningful, and thus the analyst must wait until all the free or liberated D-galactose has been fully converted to D-galactonic acid and NADH, i.e. when there is no further absorbance increase at 340 nm (see FIG. 1).

The currently available commercial enzymatic kits designed primarily for the measurement of free D-galactose and lactose, also enable the quantification of L-arabinose, according to equation 3.

$$\text{L-Arabinose} + \text{NAD}^+ \xrightarrow{(\beta\text{-galactose dehydrogenase})} \text{L-arabinonic acid} + \text{NADH} + \text{H}^+ \quad (3)$$

Limitations of All Current Products for the Determination of Free D-Galactose and/or L-Arabinose

We have discovered that all current methodologies that ultimately measure free D-galactose and/or L-arabinose, or these monosaccharides as released (or synthesized) from other molecules, such as lactose, D-galactose-1-phosphate, galactosyl-sucrose oligosaccharides (such as raffinose), galactan, galactomannan, arabinan and arabinogalactan, with NAD$^+$ and β-galactose dehydrogenase, are severely limited by the fact that the rate determining step of approach to the endpoint of the reaction is formation of the β-anomer of the sugar from the α-anomer, via the process of mutarotation. Although mutarotation from one anomer to another with some sugars is very rapid, the inter-conversion of α-galactose and β-galactose is relatively slow. The ratio of α-galactose to β-galactose where mutarotation is allowed to take place until an equilibrium is achieved, is approximately 3:7. Thus, during a D-galactose determination reaction, there is a very rapid oxidation of the β-galactose in the sample by β-galactose dehydrogenase, followed by a very slow, "mutarotation dependent", conversion of the remaining approximately 30% of D-galactose that is in the α-anomeric form; using the level of β-galactose dehydrogenase employed in traditional kits, as soon as chemical mutarotation takes place, the majority of the β-galactose product is immediately converted to D-galactonic acid and NADH. Thus, above a certain point, regardless of how much more β-galactose dehydrogenase is employed in the assay, the total reaction time will always effectively remain the same, as the limiting factor is the non-enzymatic conversion of the α-anomer into that of the β-anomer (see FIG. 1). This prevents the commonly used strategy, of adding more of a readily available/inexpensive enzyme to a reaction in order to increase the speed of an enzymatic determination, being employed. This fundamental "limitation" in the quantitative determination of free D-galactose and/or L-arabinose, or these monosaccharides as released (or synthesized) from other molecules, such as lactose, D-galactose-1-phosphate, galactosyl-sucrose oligosaccharides (such as raffinose), galactan, galactomannan, arabinan and arabinogalactan, has not previously been described anywhere in the literature, most likely because of the high cost of β-galactose dehydrogenase. However, the availability of inexpensive recombinant β-galactose dehydrogenase (i.e. Megazyme product E-GALDH), now makes it possible to incorporate much more of this enzyme into the assay, and thus the ability to overcome the fundamental mutarotation hurdle is currently of very great value.

Example 2

Assay Kit Based on Galactose Mutarotase

This invention describes a simple technique that can be universally applied to efficiently overcome the fundamental mutarotation hurdle presented when measuring free D-galactose and/or L-arabinose, or these monosaccharides as released (or synthesized) from other molecules, such as lactose, D-galactose-1-phosphate, galactosyl-sucrose oligosaccharides (such as raffinose), galactan, galactomannan, arabinan and arabinogalactan, with all existing enzymatic assay kit products based on β-galactose dehydrogenase and NAD+. As the cause of the very slow approach to the endpoint of all existing enzymatic test kits for free D-galactose and/or L-arabinose, is the conversion of α-D-galactose into β-D-galactose (or the same interconversions of L-arabinose anomers) by non-enzymatic mutarotation, by incorporating galactose mutarotase (an enzyme that specifically catalyses the same inter-conversions; synonyms: mutarotase, aldose mutarotase, galactose-1-epimerase, aldose-1-epimerase) into the assay system (see equation 4), the time taken to reach the endpoint of the reaction can be dramatically and efficiently reduced (see FIGS. 1 and 2).

(4)

Figure 2:
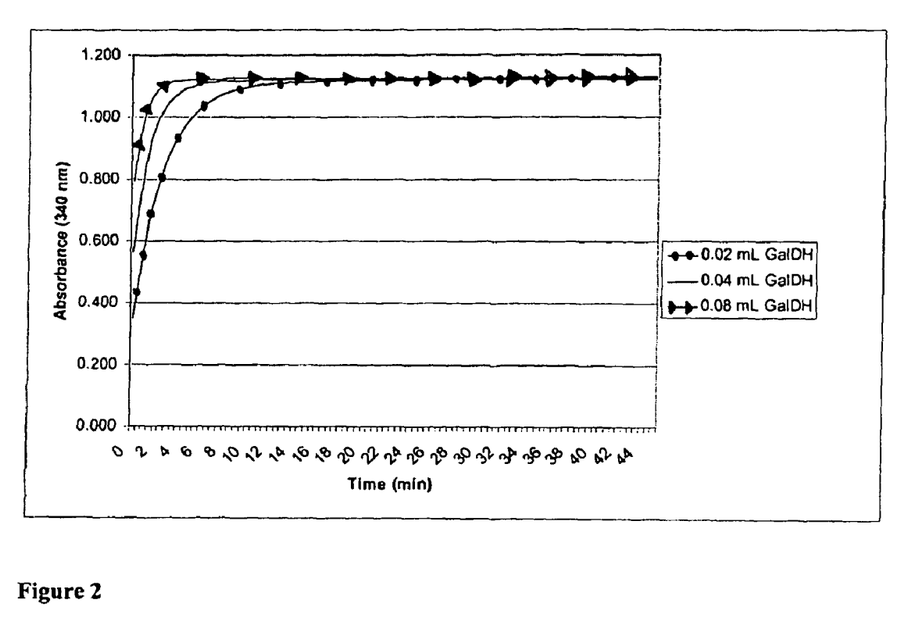
FIG. 2: shows the effect of increasing amounts of β-galactose dehydrogenase in the presence of 0.02 mL galactose mutarotase in a lactose assay.
Figure 4:
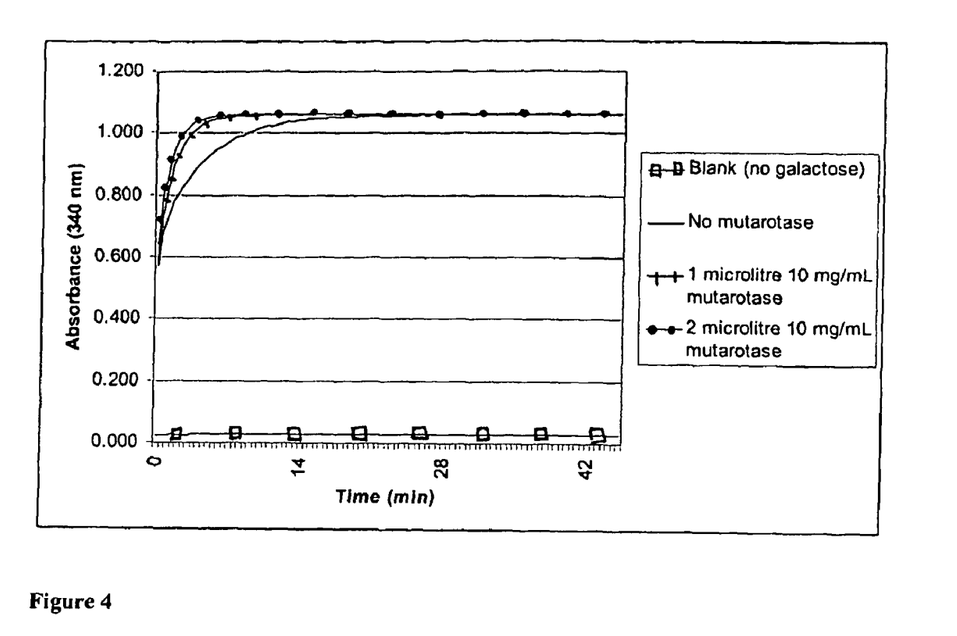
FIG. 4: shows the effect of varying amounts of Biozyme mutarotase in a Megazyme Lactose/D-Galactose Kit using Megazyme standard solution.

For instance, when galactose mutarotase GalM from *E. coli* is incorporated into the assay system as defined by equations 5 and 6, the addition of increasing amounts of β-galactose dehydrogenase does now result in a respective decrease in the amount of time required to reach the end point of the reaction (see FIG. 2). However, it is important to note that any galactose mutarotase could be employed in this application, for instance the galactose mutarotase termed "mutarotase" supplied by Biozyme Laboratories Limited, works equally as well (see FIG. 4). This enzyme is offered by many suppliers, is purified from porcine kidney, and although is commonly referred to as "mutarotase", is more formally a galactose mutarotase.

EXPERIMENTAL DEMONSTRATION

The following experiment was performed to demonstrate the effect of addition of GalM from *E. coli* to the assay system, comprising equations 5 and 6 below, for the quantification of free D-galactose:

(5)

(6)

The reaction mixtures comprised:

0.2 mL of 2 M Tris/HCl buffer, pH 8.6 containing 40 mM EDTA 0.1 mL of 8 mg/mL NAD+

0.2 mL of 0.5 (assays 1-7) or 0.4 (assays 8-10) mg/mL D-galactose 0.00-0.02 mL of GalM from *E. coli*

0.02-0.08 mL of β-galactose dehydrogenase at 100 U/mL 2.12-2.20 mL of deionised $H_2O$ The reactions were performed at 25.8° C., and a summary of the results is presented in Table 1.

RESULTS AND CONCLUSIONS

TABLE 1

The effect on the time taken to reach the endpoint of the reaction when varying the levels of galactose mutarotase (GalM) and β-galactose dehydrogenase.

| Assay | mL of GalM | mL of β-galactose dehydrogenase | Endpoint of the reaction (minutes) |
|---|---|---|---|
| 1 | 0.02 | 0.08 | ~3 |
| 2 | 0.02 | 0.06 | ~4 |
| 3 | 0.02 | 0.04 | ~6 |
| 4 | 0.02 | 0.02 | ~9 |
| 5 | 0.01 | 0.02 | ~9 |
| 6 | 0.00 | 0.02 | — |
| 7 | 0.00 | 0.02 | >20 |
| 8 | 0.00 | 0.02 | ~36 |
| 9 | 0.00 | 0.04 | ~28 |
| 10 | 0.00 | 0.08 | ~24 |

Figure 3:
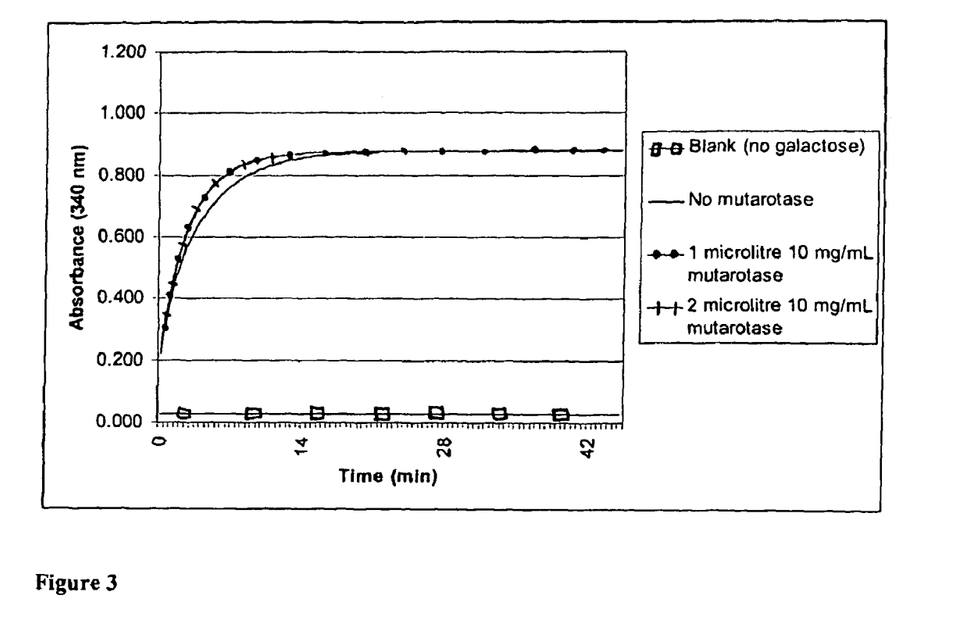
FIG. 3: shows the effect of varying amounts of Biozyme mutarotase in a SCIL Lactose/D-Galactose Kit using Megazyme standard solution.

From this simple experiment, it can be seen that when the amount of β-galactose dehydrogenase in the assay is kept the same at 0.02 mL, and the level of GalM is increased from 0.00 mL to 0.01 or 0.02 mL (assays 7, 5 and 4, respectively), the endpoint is reached in less than half the time, i.e. approximately 9 minutes as opposed to >20 minutes. It can also be seen that if the amount of β-galactose dehydrogenase in the assay is increased progressively from 0.02 to 0.08 mL (assays 4, 3, 2 and 1, respectively), while keeping the level of GalM the same at 0.02 mL, the endpoint is reached progressively faster (improving from approximately 9 minutes to approximately 3 minutes). When using 0.02 mL of GalM and 0.08 mL of β-galactose dehydrogenase, the endpoint is reached in approximately 3 min at 25.8° C. Other commercial products for the measurement of D-galactose, that do not incorporate GalM, would take approximately 30 minutes to perform the same reaction (see FIG. 3).

It should be noted that the levels of both GalM and β-galactose dehydrogenase required to achieve the 3 minute endpoint reaction above are commercially viable quantities of these reagents, and in both cases would not lead to any deleterious effects on the performance of the assay.

Specificity of Galactose Mutarotase

Galactose mutarotase is active on D-galactose, L-arabinose, D-xylose, maltose, lactose, D-fucose, D-fructose and D-glucose. However, an assay system incorporating galactose mutarotase has only been described for the determination of glucose with glucose oxidase; for instance, there are accounts of the use of "mutarotase" from pig (porcine) kidney to convert α-D-glucose into β-D-glucose to act as a substrate for glucose oxidase, that only recognizes the β-anomer (for examples see equations 7, 8 and 9). However, there are no accounts of the requirement to convert α-D-galactose into β-D-galactose, or α-L-arabinose into β-L-arabinose, or the means of doing so, or the potential applications thereof.

Due to the broad specificity of galactose mutarotase, it may be possible to use this assay protocol for other sugars in addition to D-galactose and L-arabinose, such as D-xylose, maltose, lactose, D-fucose, and D-fructose, using appropriate dehydrogenases.

There are many suppliers of the enzyme termed "mutarotase" from porcine kidney, e.g. Roche, Biozyme, Calzyme, and Calbiochem. There are, however, no commercial suppliers of the enzyme termed "galactose mutarotase" (GalM) from *E. coli*, though this enzyme has been biochemically characterized in the literature and the corresponding gene identified as galM. This gene has been cloned by Megazyme and active recombinant protein produced that possesses the necessary biochemical characteristics for this invention (see "Experimental Demonstration" section above).

POTENTIAL APPLICATIONS OF THE INVENTION

The primary applications of this invention include (1) the rapid measurement of free D-galactose, and D-galactose as released by β-galactosidase from lactose, in milk, dairy products and many other materials, and (2) the rapid measurement of free D-galactose and D-galactose as released by phosphatase from D-galactose-1-phosphate, in the blood of newborn babies, as a diagnostic test for Galactos(a)emia. As can be seen from FIG. 3, the addition of galactose mutarotase to competitor products that contain β-galactose dehydrogenase, as would be expected, speeds up the determination of D-galactose.

There are however many other applications involving the measurement of principally, though not exclusively, free D-galactose and/or L-arabinose, or these monosaccharides as released (or synthesized) from other molecules, such as lactose, D-galactose-1-phosphate, galactosyl-sucrose oligosaccharides (such as raffinose), galactan, galactomannan, arabinan and arabinogalactan. Applications include the rapid assay of the following analytes:

(a) Lactose (e.g. in milk, cheese, dairy products, foods for the lactose intolerant, etc; see following reaction scheme):

(b) D-Galactose (e.g. in blood, milk, etc; see following reaction scheme):

(c) D-Galactose-1-phosphate (e.g. in blood; see following reaction scheme):

(d) L-Arabinose (e.g. as a sweetener in foods and beverages, and in pharmaceuticals, vegetables, fruit, wine, etc; see following reaction scheme):

(e) D-Galactose after release from galactan (see following reaction scheme):

(galactanase, galactosidase and/or other enzyme(s) if required) (or chemical hydrolysis)

(f) D-Galactose after release from galactomannan (see following reaction scheme):

(g) D-Galactose after release from galactooligosaccharides (see following reaction scheme):

(h) D-Galactose after release from complex molecules, e.g. glycoproteins (see following reaction scheme):

(i) D-Galactose after release from lactulose (see following reaction scheme):

(32)

Lactulose + H₂O —(galactosidase, and/or other enzyme(s) if required) (or chemical hydrolysis)→ D-galactose + D-fructose (33)

α-D-Galactose ⇌(galactose mutarotase)⇌ β-D-galactose (34)

β-D-Galactose + NAD⁺ —(β-galactose dehydrogenase)→ D-galactonic acid + NADH + H⁺

(j) D-Galactose and L-arabinose after release from arabinogalactan (see following reaction scheme):

(35)

Arabinogalactan + H₂O —(arabinanase, arabinofuranosidase, galactanase, galactosidase, and/or other enzyme(s) if required) (or chemical hydrolysis)→ D-galactose + L-arabinose (36)

α-L-Arabinose ⇌(galactose mutarotase)⇌ β-L-arabinose (37)

α-D-Galactose ⇌ β-D-galactose (38)

β-D-Galactose + NAD⁺ —(β-galactose dehydrogenase)→ D-galactonic acid + NADH + H⁺

(39)

β-L-Arabinose + NAD⁺ ⟶ D-arabinonic acid + NADH + H⁺

(k) D-Galactose after release from galactobiose (see following reaction scheme):

(40)

Galactobiose + H₂O —(galactosidase, and/or other enzyme(s) if required) (or chemical hydrolysis)→ 2 D-galactose

(41)

α-D-Galactose ⇌(galactose mutarotase)⇌ β-D-galactose

(42)

β-D-Galactose + NAD⁺ —(β-galactose dehydrogenase)→ D-galactonic acid + NADH + H⁺

(l) L-Arabinose after release from arabinoxylan (see following reaction scheme):

(m) L-Arabinose after release from arabinan (e.g. in fruit juice manufacture; see following reaction scheme):

(n) L-Arabinose after release from complex molecules, e.g. glycoproteins (see following reaction scheme):

(o) L-Arabinose after release from arabinooligosaccharides (see following reaction scheme):

(p) L-Arabinose after release from arabinobiose (see following reaction scheme):

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. An assay kit for measuring free D-galactose and/or L-arabinose in a sample, the kit comprising galactose mutarotase and β-galactose dehydrogenase.

2. The assay kit as claimed in claim 1 further comprising $NAD^+$.

3. The assay kit as claimed in claim 1 wherein the galactose mutarotase is selected from the group consisting of GalM derived from *E. coli*, porcine kidney mutarose, or mutarotase which catalyzes interconversion of α- and β-D-galactose and/or α- and β-L-arabinose.

4. The assay kit as claimed in claim 1 further comprising a hydrolyzing reagent which hydrolyzes molecules containing D-galactose and/or L-arabinose, to yield the free mono- or di-saccharide.

5. The assay kit as claimed in claim 4 wherein the hydrolyzing reagent comprises at least one enzyme which releases free D-galactose and/or L-arabinose from larger molecules, or assists other enzymes in so releasing D-galactose and/or L-arabinose.

6. The assay kit as claimed in claim 5 wherein the enzyme(s) is selected from the group consisting of β-galactosidase, β-galactanase, α-galactosidase, endo-arabinanase, exo-arabinanase, α-L-arabinofuranosidase, acid phosphatase, alkaline phosphatase, β-mannanase, β-mannosidase, β-xylanase, α-glucuronidase, esterase, and xylan acetyl-esterase.

7. The assay kit as claimed in any preceding claim further comprising at least one buffer, in the pH range 4.0 to 10.0.

8. The assay kit as claimed in claim 7 wherein the buffer is Tris/HCl buffer containing EDTA.

9. The assay kit as claimed in claim 1 comprising sufficient galactose mutarotase to give at least 0.1 μg/mL in the final assay mixture.

10. The assay kit as claimed in claim 9 comprising sufficient galactose mutarotase to give at least 1 μg/mL in the final assay mixture.

11. The assay kit as claimed in claim 9 or 10 comprising sufficient galactose mutarotase to give at least 3 μg/mL in the final assay mixture.

12. The assay kit as claimed in claim 1 for determination of free D-galactose and/or L-arabinose as released or synthesized by an enzymatic reaction and/or by chemical hydrolysis from other molecules selected from the group consisting of lactose, D-galactose-1-phosphate, galactosyl-sucrose oligosaccharides, raffinose, galactan, galactomannan, arabinan and arabinogalactan.

* * * * *